(12) United States Patent
Ahrens et al.

(10) Patent No.: US 6,663,634 B2
(45) Date of Patent: Dec. 16, 2003

(54) BONE SCREW

(75) Inventors: Michael Ahrens, Hamburg (DE); Urs Schlegel, Davos Plantz (CH); Silvia Beer, Beringen (CH)

(73) Assignee: Synthes (U.S.A.), Paoli, PA (US)

( * ) Notice: Subject to any disclaimer, the term of this patent is extended or adjusted under 35 U.S.C. 154(b) by 168 days.

(21) Appl. No.: 09/920,730

(22) Filed: Aug. 3, 2001

(65) Prior Publication Data

US 2002/0029043 A1 Mar. 7, 2002

Related U.S. Application Data

(63) Continuation of application No. PCT/CH99/00049, filed on Feb. 4, 1999.

(51) Int. Cl.$^7$ ............................................... A61B 17/56
(52) U.S. Cl. ........................................... 606/73; 606/76
(58) Field of Search .............................. 606/60, 61, 65, 606/67, 72, 73, 76

(56) References Cited

U.S. PATENT DOCUMENTS

| 4,476,590 A | 10/1984 | Scales et al. |
| 5,108,399 A | 4/1992 | Eitenmuller et al. |
| 5,759,564 A | 6/1998 | Milder et al. |
| 5,770,255 A | 6/1998 | Burrell et al. |
| 5,906,600 A | 5/1999 | Bähr |

FOREIGN PATENT DOCUMENTS

| CH | 657519 | 9/1986 |
| EP | 0792 654 A3 | 9/1997 |
| WO | WO 89/04674 | 6/1989 |

*Primary Examiner*—Eduardo C. Robert
(74) *Attorney, Agent, or Firm*—Pennie & Edmonds LLP

(57) ABSTRACT

A bone fastener which prevents infection that can be used, for example, to attach an external fixation device to bone. The fastener may be partially coated with an antibacterial agent (such as silver) directly deposited on the biocompatible material to prevent infection. The coating can be applied to the fastener in a number of different ways in a wide variety of patterns.

40 Claims, 3 Drawing Sheets

BONE SCREW

CROSS-REFERENCE TO RELATED APPLICATIONS

This application is a continuation of the U.S. national stage designation of copending International Patent Application PCT/CH99/00049, filed Feb. 4, 1999, the entire content of which is expressly incorporated herein by reference thereto.

FIELD OF THE INVENTION

The present invention relates generally to orthopaedic screws or pins, and in particular to a bone screw having antimicrobial activity.

BACKGROUND OF THE INVENTION

Infection frequently accompanies the use of external bone fastening or fixation systems having screws or pins (hereafter "screws"), which are implanted through soft tissue and into bone. For instance, bone screws may entail infection in soft-tissue by introducing microorganisms into an operation wound. Commonly known as pin-tract infection ("PTI"), these infections may further affect the bone. Accordingly, medical devices which are implanted through soft tissue have been developed with antibacterial effects to prevent infection.

One bone screw known from the related art is disclosed in Swiss Patent No. 657,519 to Blaettler. Based on the already long known antibacterial effect of silver, the '519 patent teaches a surgical implant which is silver-coated. The silver coating is not deposited directly on the substrate, rather, it is deposited on an intermediate copper layer. This allows the concentration of silver ions to reach levels (typically about 1.42 $\mu$g/ml), which may inhibit osteoblasts, thereby limiting the formation of new bone.

Another medical device known from the related art is disclosed in U.S. Pat. No. 5,759,564 which teaches a catheter comprising an iontophoretic material and a structure for medical devices that reduces infection by killing microorganisms with controlled oligodynamic iontophoresis. Iontophoresis is the movement of ions in a conductive fluid under the influence of low-strength electric fields.

Additionally, U.S. Pat. No. 5,108,399 discloses a resorbable screw or threaded bolt for fixation of a bone plate and teaches a resorbable screw having a synthetic film comprising collodially distributed silver for preventing infection. This screw, however, is not structurally suitable for use with an external fixation device.

Also, U.S. Pat. No. 5,906,600 discloses an antimicrobial plastic tube or synthetic hose having a silver coating. A slit extending over the entire length of the device allows the hose to be radially pushed (or slipped) onto an orthopedic fastening element so that the antimicrobial effect of the hose surround these pieces. The antimicrobial hose, however, increases trauma to the patient because a longer incision is required to insert the surrounded fastening element through the incision and soft tissue near a bone. The antimicrobial hose also incurs the disadvantage of not being capable of being sterilized and reused.

Despite these developments, a need exists for a bone screw having antibacterial activity that is particularly adapted for use in an external fixation system and which precludes infection.

SUMMARY OF THE INVENTION

The present invention is directed to a bone pin formed of a biocompatible material and comprising a first portion located at a distal end of the pin and having a threaded section for insertion into bone and a second portion located at a proximal end of the pin. In an exemplary embodiment of the bone pin, the threaded section is at least 3 mm in length and the second portion has a length between 2 cm and 3 cm.

The bone pin also comprises a third portion located between the first and second portions, which is at least partially coated with an antibacterial agent directly deposited on the biocompatible material free of any intermediate layer. The antibacterial agent is non-colloidal silver, and the biocompatible material is selected from a group consisting of steel, titanium, tantalum, and niobium. Alternatively, the biocompatible material may be selected from a group consisting of polylactides, polyurethanes, hydroxyapatites, glasses, ceramics, and carbon fibers.

The silver may be electrochemically deposited on the biocompatible material, or may comprise a foil deposited on the biocompatible material. In general, the antibacterial agent covers at least 10 percent of the bone pin surface area and forms a layer having a thickness of at least about 10 $\mu$m. In one embodiment of the present invention, the antibacterial agent forms a plurality of rings spaced axially along the third portion. In another embodiment, the antibacterial agent forms a plurality of strips spaced radially about at least a part of the third portion.

The present invention also relates to a method for external fixation of a bone comprising the steps of threadably inserting the first portion of a bone pin according to the present invention into a bone and applying an electric current to the bone pin to stimulate formation of new bone and increase infection resistance of the antibacterial agent. In one embodiment of the method, the electric current is 0.25 $\mu$A. In another embodiment, the electric current is between 5 and 20 $\mu$A.

Essentially, the general advantages offered by the present invention include use of the bone screw without a silver coating and in a fully conventional manner; re-use following preparation and sterilization; and acts as a prophylaxis against infection. This prophylactic effect can be significant when there is shortage of drugs, for example, in developing countries.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
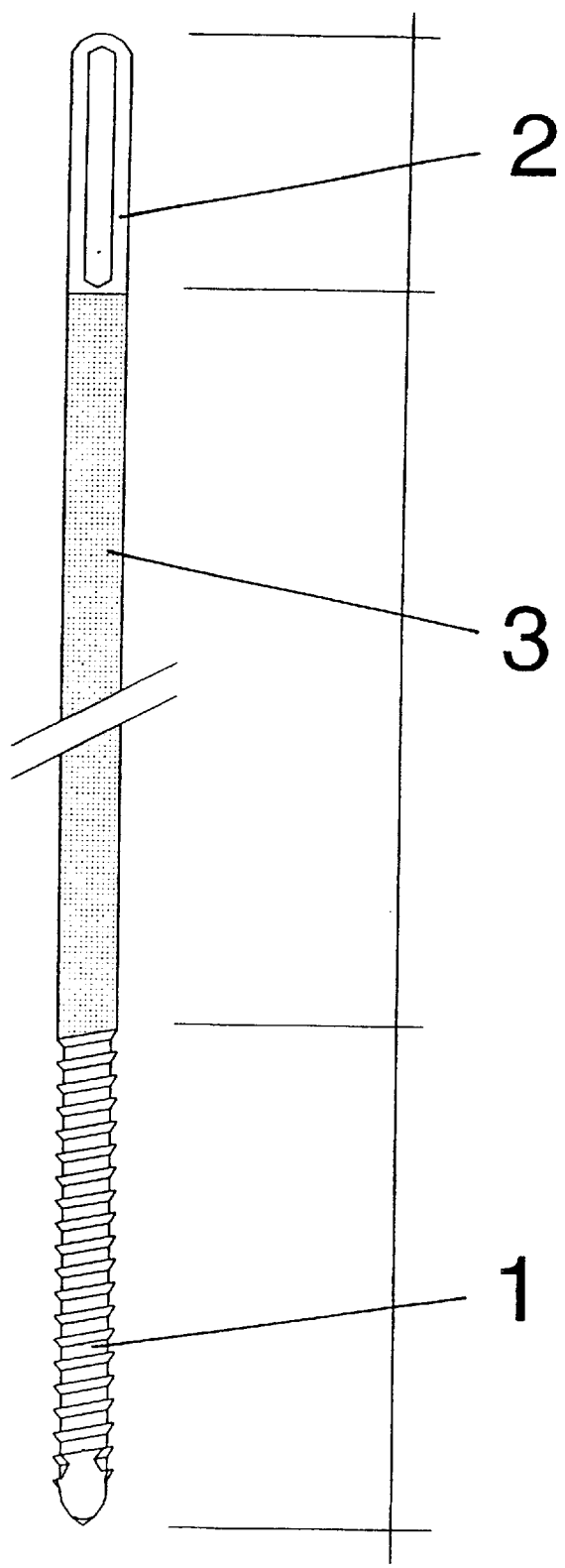
FIG. 1 is a partial elevation view of a bone screw according to the present invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

Figure 2:
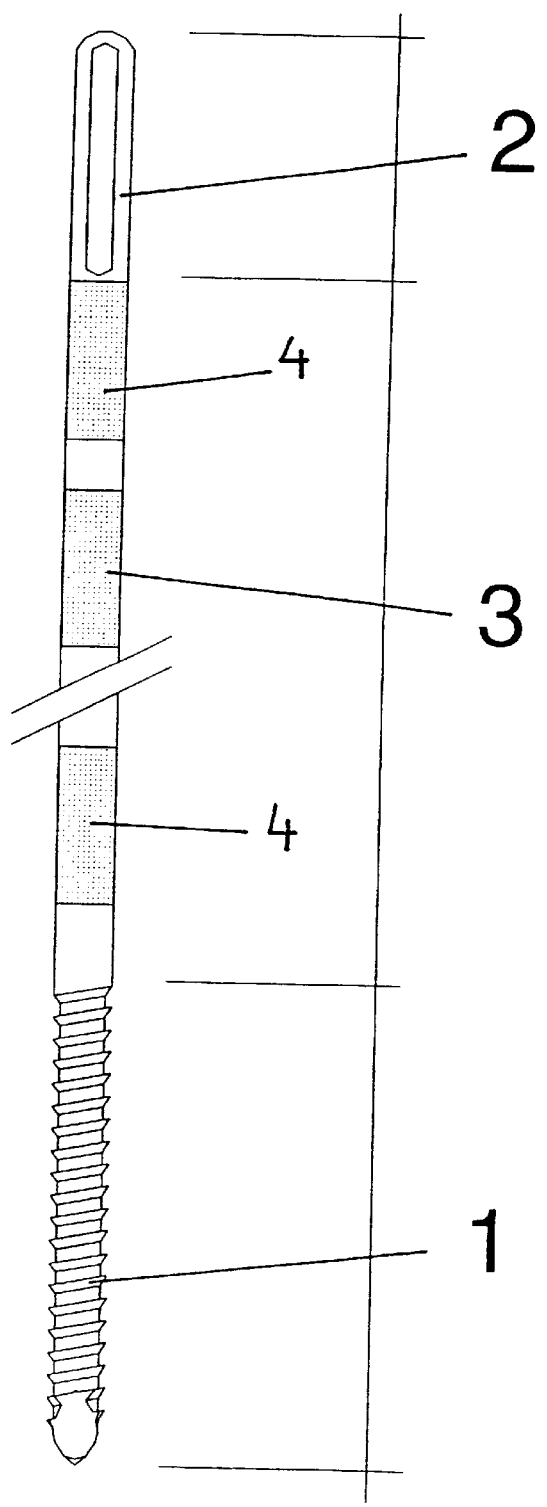
FIG. 2 is a partial elevation view of another embodiment of the bone screw according to the present invention.
Figure 3:
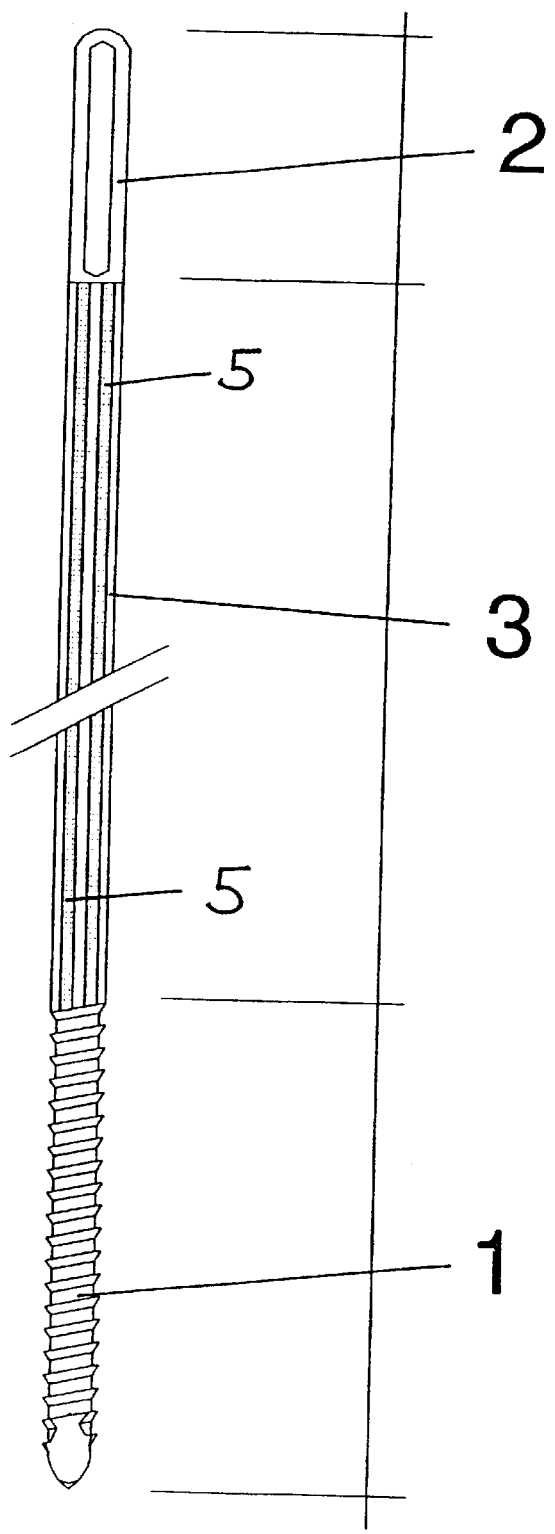
FIG. 3 is a partial elevation view of another embodiment of the bone screw according to the present invention.

Referring to FIGS. 1–3, a bone screw according to the present invention is provided with front 1 and rear 2 portions and an intermediate shank portion 3. In the illustrative embodiments shown in FIGS. 1–3, front portion 1 is threaded. Rear portion 2 and intermediate shank portion 3 are not threaded. The bone screw according to the invention is formed from steel, titanium, or other biocompatible materials. Examples of such materials include, without limitation, tantalum, niobium, polylactides, polyurethanes, hydroxyapatites, glasses, ceramics and carbon fibers.

Referring to FIG. 1, this embodiment of the present invention shows an intermediate shank portion 3 which is silver coated, and front 1 and rear portions 2 which are not silver coated. The threaded portion 1 is not coated with silver because direct contact of silver with bone may inhibit osteoblasts. The rear portion 2 of the screw which may be externally and mechanically stressed by clamping jaws of a fastening system is also uncoated.

As previously noted, the bone screw is only partly coated with silver, namely at least in the portion 3 of the shank which contacts the soft-tissue parts that are to be protected against infection. Because of the coating, galvanic currents arise only at the surfaces between the rear portion 2 and the shank portion 3 and between the shank portion 3 and the front portion 1. The results are a bactericidal emission of silver ions in the coated regions of the screw and the growth of osteoblasts, which are stimulated in regions lacking silver coating.

If a bone screw according to the present invention is made of titanium or a typical surgical grade steel (for instance a Cr Ni Mo steel per ISO 58/32-1 with 16% chromium, 13% nickel, 3% molybdenum and 68% iron), because of the different positions of the elements molybdenum (−0.2 v), nickel (−0.24 v), iron (−0.447 v), chromium (0.744 v) and titanium (−1.63 v) relative to silver (+0.8 v) in the electrochemical series, there will be a difference of at least 1 v (for 1 g of ion dissolved in 1 ltr of solution at 25° C.) for a FeNi substrate. In this configuration, the silver coating is the anode and the steel (or titanium) is the cathode. Experiments with bacteria have shown that bactericidal effects take place predominantly at the anode. Electric current stimulation applied to bone fractures were found at the bone cells at the cathode. The anti-bacterial effect of a bone screw according to the invention may be further raised by applying a weak electric current across the cell, for instance about 0.25 $\mu$A. A current of about 5 to 20 $\mu$A, typically, may be used at about 0.8 V.

The thickness of the silver coating can be greater than about 10 $\mu$m, and the coated surface Sag can be about 10% of the total surface $S_{tot}$ of the bone screw. The silver coating may be deposited either electrochemically or as a metal foil free of any intermediate layer on the biocompatible material. Another way is to bond the silver coating to the biocompatible material. Processes which may be used to create a silver coatings on the screw include, without limitation, electrochemical anodization, ion assisted beam deposition (IADB), and using a foil with conducting and non-conducting adhesives. The coating-free zones may be covered by masks during these processes.

Referring to FIGS. 1–3, the threaded front portion 1 can be at least about 3 mm long to assure adequate anchoring in the bone. Typically, the rear portion 2 of the bone screw can be 2 to 3 cm long because the chuck of the drill used to drive in the pin requires about 2 cm to clamp the pin and another 1 cm should remain free of silver to prevent mechanical abrasion from the jaws of pin clamp and the zone of the drill chuck. Further, there is no need for a silver coating at the end of the pin in which there is no contact with underlying soft tissue and the skin.

Referring to FIGS. 2 and 3, these illustrative embodiments of the present invention differ from the screw of FIG. 1 in the configuration of the intermediate shank portion 3. In these embodiments, the bone screws are provided with a silver coating only partly in the intermediate portion of the shank. For instance, in the embodiment shown in FIG. 2, the intermediate shank portion 3 is provided with silver-coated segments or rings 4 spaced from one another in the axial direction. In the embodiment shown in FIG. 3, the intermediate shank portion 3 is provided with silver-coated longitudinal strips 5. In these embodiments, the galvanic cell is situated within the intermediate shank portion 3, and results in uniform emission of silver ions to soft-tissue and providing infection prophylaxis. Because the charge differential across the galvanic cell decreases with time and the quantity of exchanged ions, a predetermined quantity of silver ions can be emitted. While this may preclude sterilizing the pins for reuse, it allows for the controlled emission of silver ions.

While various descriptions of the present invention are described above, it should be understood that the various features can be used singly or in any combination thereof. Therefore, this invention is not to be limited to only the specifically preferred embodiments depicted herein. For instance, the length of the rear portion may be adjusted to accommodate different drill or fastening systems. Similarly, other coating patterns in the intermediate shank portion may be used.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A bone pin formed of a biocompatible material comprising:
   a first portion located at a distal end of the pin having a threaded section for insertion into bone;
   a second portion located at a proximal end of the pin; and
   a third portion located between the first and second portions,
   wherein the third portion is at least partially coated with an antibacterial agent directly deposited on the biocompatible material free of any intermediate layer, and the antibacterial agent forms a plurality of rings spaced axially along the third portion.

2. The bone pin of claim 1, wherein the antibacterial agent comprises silver.

3. The bone pin of claim 2, wherein the silver is non-colloidal.

4. The bone pin of claim 3, wherein the antibacterial agent covers at least about 10 percent of the bone pin surface area.

5. The bone pin of claim 4, wherein the antibacterial agent forms a layer having a thickness of at least about 10 $\mu$m.

6. The bone pin of claim 5, wherein the threaded section is at least about 3 mm in length.

7. The bone pin of claim 2, wherein the silver is electrochemically deposited on the biocompatible material.

8. The bone pin of claim 2, wherein the silver comprises a foil adhered to the biocompatible material.

9. The bone pin of claim 2, wherein the second portion has a length between about 2 cm and about 3 cm.

10. The bone pin of claim 2, wherein the biocompatible material is selected from the group consisting of steel, titanium, tantalum, and niobium.

11. The bone pin of claim 2, wherein the biocompatible material is selected from the group consisting of polylactides, polyurethanes, hydroxyapatites, glasses, ceramics, and carbon fibers.

12. The bone pin of claim 1, wherein the antibacterial agent forms a plurality of strips spaced radially about at least a part of the third portion.

13. A method for external fixation of a bone comprising the steps of:
   threadably inserting the first portion of at least one bone pin of claim 1 into a bone; and
   applying an electric current to the at least one bone pin to stimulate formation of new bone and increase infection resistance of the antibacterial agent.

14. The method of claim 13, wherein the electric current is about 0.25 µA.

15. The method of claim 13, wherein the electric current is between about 5 µA and about 20 µA.

16. An orthopedic fastener having a longitudinal axis comprising:
   a distal end having threads for anchoring the fastener into bone;
   a proximal end having an attachment site for an orthopedic instrument; and
   a bactericidal shank having an outer surface for contacting soft tissue, the outer surface of the shank formed from a biocompatible material that is at least partially coated with an antibacterial agent, the antibacterial agent forming a plurality of segments on the biocompatible material for selectively treating the soft tissue,
   wherein the biocompatible material and the antibacterial agent are adapted to selectively release the antibacterial agent in-vivo and provide infection prophylaxis for the soft tissue.

17. The fastener of claim 16, wherein the segments comprise a pattern.

18. The fastener of claim 17, wherein the pattern comprises at least two bands.

19. The fastener of claim 18, wherein the bands form two or more rings spaced axially along the shaft.

20. The fastener of claim 18, wherein the pattern comprises a plurality of bands aligned with the longitudinal axis.

21. The fastener of claim 16, wherein the threads are not coated with the antibacterial agent.

22. The fastener of claim 21, wherein the attachment site is not coated with the antibacterial agent.

23. The fastener of claim 16, wherein the attachment site comprises a bore in the biocompatible material.

24. The fastener of claim 23, wherein the bore comprises an elongate hole extending through the fastener.

25. The fastener of claim 16, wherein the orthopedic instrument comprises an external fixation system.

26. The fastener of claim 16, wherein the orthopedic instrument comprises a drill or a screwdriver.

27. The fastener of claim 16, further comprising an external fixation system configured and dimensioned to attach to the attachment site.

28. The fastener of claim 16, wherein the antibacterial agent comprises a silver foil, a conducting adhesive, and a non conducting adhesive.

29. The fastener of claim 16, wherein the antibacterial agent comprises an anodized coating.

30. The fastener of claim 16, wherein the coating comprises an ion assisted beam deposition.

31. The fastener of claim 16, wherein the antibacterial agent comprises silver.

32. The fastener of claim 31, wherein the silver is non colloidal.

33. The fastener of claim 32, wherein the antibacterial agent covers at least 10 percent of the fastener surface area.

34. The fastener of claim 33, wherein the antibacterial agent forms a layer having a thickness of at least about 10 µm.

35. The fastener of claim 33, wherein the threads for anchoring the fastener into one comprise a length of at least about 3 mm.

36. The fastener of claim 33, wherein the attachment site at the proximal end of the fastener comprises a length between about 2 cm and about 3 cm.

37. The fastener of claim 33, wherein the biocompatible material is selected from the group consisting of polylactides, polyurethanes, hydroxyapatites, glasses, ceramics, and carbon fibers.

38. The fastener of claim 37, wherein the biocompatible is selected from the group consisting of steel, titanium, tantalum, and niobium.

39. The fastener of claim 38, wherein the biocompatible material comprises a surgical grade steel.

40. An orthopedic fastener having a longitudinal axis comprising:
   a distal end having threads for anchoring the fastener into bone;
   a proximal end having an attachment site for an orthopedic instrument; and
   a bactericidal shank having an outer surface for contacting soft tissue, the outer surface of the shank formed from a biocompatible material that is at least partially coated with an antibacterial agent,
   wherein the biocompatible material and the antibacterial agent are adapted to selectively release the antibacterial agent in-vivo and provide infection prophylaxis for the soft tissue and the threads are not coated with the antibacterial agent.

* * * * *